United States Patent
Vija et al.

(10) Patent No.: US 11,704,795 B2
(45) Date of Patent: Jul. 18, 2023

(54) QUALITY-DRIVEN IMAGE PROCESSING

(71) Applicant: Siemens Medical Solutions USA, Inc., Malvern, PA (US)

(72) Inventors: Alexander Hans Vija, Evanston, IL (US); Francesc dAssis Massanes Basi, Chicago, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 141 days.

(21) Appl. No.: 16/946,214

(22) Filed: Jun. 10, 2020

(65) Prior Publication Data
US 2021/0110535 A1    Apr. 15, 2021

Related U.S. Application Data

(60) Provisional application No. 62/912,824, filed on Oct. 9, 2019.

(51) Int. Cl.
| | | |
|---|---|---|
| G06T 7/00 | (2017.01) | |
| G06T 11/00 | (2006.01) | |
| G06T 7/11 | (2017.01) | |
| G06T 5/00 | (2006.01) | |
| G06T 5/20 | (2006.01) | |

(52) U.S. Cl.
CPC ............ *G06T 7/0012* (2013.01); *G06T 5/002* (2013.01); *G06T 5/20* (2013.01); *G06T 7/11* (2017.01); *G06T 11/008* (2013.01); *G06T 2207/10081* (2013.01); *G06T 2207/10088* (2013.01); *G06T 2207/30004* (2013.01); *G06T 2207/30168* (2013.01); *G06T 2211/424* (2013.01)

(58) Field of Classification Search
CPC ......... G06T 7/0012; G06T 7/11; G06T 5/002; G06T 5/20; G06T 11/008; G06T 2207/10081; G06T 2207/10088; G06T 2207/30004; G06T 2207/30168; G06T 2211/424
See application file for complete search history.

(56) References Cited

U.S. PATENT DOCUMENTS

| | | | |
|---|---|---|---|
| 2006/0210131 A1* | 9/2006 | Wheeler, Jr. .......... | G06T 11/008 382/128 |
| 2010/0014732 A1* | 1/2010 | Vija ........................ | G06T 5/001 382/280 |
| 2010/0098309 A1* | 4/2010 | Graessner ............... | G06F 18/00 382/131 |

(Continued)

OTHER PUBLICATIONS

Vunckx K, Suetens P, Nuyts J. Effect of overlapping projections on reconstruction image quality in multipinhole SPECT. IEEE transactions on medical imaging. Jun. 24, 2008;27(7):972-83. (Year: 2008).*

*Primary Examiner* — Edward F Urban
*Assistant Examiner* — Duy Tran

(57) ABSTRACT

A framework for quality-driven image processing. In accordance with one aspect, image data and anatomical data of a region of interest are received. Zonal information is generated based on the anatomical data. Image processing is performed based on the image data to generate an intermediate image. One or more image quality metrics may then be determined for the intermediate image data using the zonal information. A processing action may be performed based on the one or more image quality metrics to generate a final image.

20 Claims, 5 Drawing Sheets

(56) References Cited

U.S. PATENT DOCUMENTS

| | | | |
|---|---|---|---|
| 2011/0298793 A1* | 12/2011 | Lauritsch | A61B 6/4458 345/419 |
| 2013/0085387 A1* | 4/2013 | Chen | A61B 8/4218 600/407 |
| 2014/0140601 A1* | 5/2014 | Litvin | G06T 11/006 382/131 |
| 2014/0369577 A1* | 12/2014 | Collins | G06F 16/583 382/128 |
| 2016/0338613 A1* | 11/2016 | Beckers | A61B 5/0263 |
| 2017/0143312 A1* | 5/2017 | Hedlund | A61B 6/487 |

* cited by examiner

QUALITY-DRIVEN IMAGE PROCESSING

CROSS-REFERENCE TO RELATED APPLICATION

The present application claims the benefit of U.S. provisional application No. 62/912,824 filed Oct. 9, 2019, the entire contents of which are herein incorporated by reference.

TECHNICAL FIELD

The present disclosure generally relates to image processing, and more particularly to a quality-driven image processing.

BACKGROUND

Nuclear tomographic imaging, particularly single photon emission computed tomography (SPECT), involves an imaging detector (e.g., a scintillation camera) rotating around the patient to obtain a plurality of data acquisitions, which are subsequently processed to reconstruct tomographic "slice" images of the patient using an iterative reconstruction method. Iterative image reconstruction methods, such as non-negative least square or likelihood algorithms, iteratively fit image models to a data set and thus calculate a final image while minimizing the effect of noise to the image.

Convergence is typically defined with respect to an objective function using some global metric. This is because although the solution of an ill-conditioned noisy inverse problem may fit the data at convergence, it may not be interpretable by the human reader who has a specific imaging task, such as detection or classification of an extended lesion in a background of finite contrast. Today, one may employ heuristic and ad-hoc termination rules-of-thumb or regularizers, with various methods to determine the strength. However, all these methods result in a set of parameters that are linked to a visual interpretation of the human observer that is often based on trial and error.

SUMMARY

Described herein are systems and methods for quality-driven image processing. In accordance with one aspect, image data and anatomical data of a region of interest are received. Zonal information is generated based on the anatomical data. Image processing is performed based on the image data to generate an intermediate image. One or more image quality metrics may then be determined for the intermediate image data using the zonal information. A processing action may be performed based on the one or more image quality metrics to generate a final image.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings.

DETAILED DESCRIPTION

Figure 1:
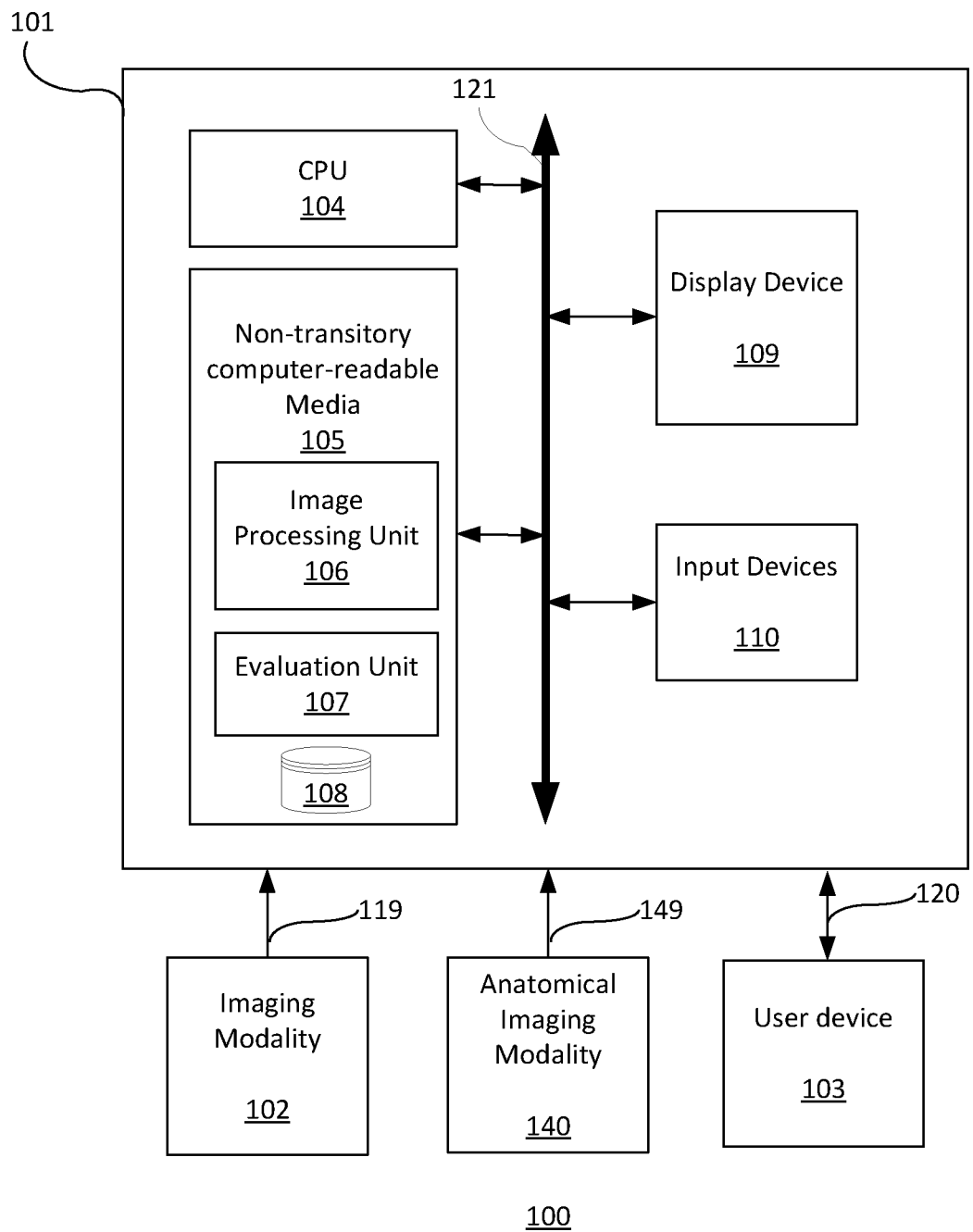
FIG. 1 is a block diagram illustrating an exemplary system.

In the following description, numerous specific details are set forth such as examples of specific components, devices, methods, etc., in order to provide a thorough understanding of implementations of the present framework. It will be apparent, however, to one skilled in the art that these specific details need not be employed to practice implementations of the present framework. In other instances, well-known materials or methods have not been described in detail in order to avoid unnecessarily obscuring implementations of the present framework. While the present framework is susceptible to various modifications and alternative forms, specific embodiments thereof are shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention. Furthermore, for ease of understanding, certain method steps are delineated as separate steps; however, these separately delineated steps should not be construed as necessarily order dependent in their performance.

The term "x-ray image" as used herein may mean a visible x-ray image (e.g., displayed on a video screen) or a digital representation of an x-ray image (e.g., a file corresponding to the pixel output of an x-ray detector). The term "in-treatment x-ray image" as used herein may refer to images captured at any point in time during a treatment delivery phase of an interventional or therapeutic procedure, which may include times when the radiation source is either on or off. From time to time, for convenience of description, CT imaging data (e.g., cone-beam CT imaging data) may be used herein as an exemplary imaging modality. It will be appreciated, however, that data from any type of imaging modality including but not limited to x-ray radiographs, MRI, PET (positron emission tomography), PET-CT, SPECT, SPECT-CT, SPECT-MR, MR-PET, 3D ultrasound images or the like may also be used in various implementations.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present framework are not described with reference to any particular programming language. It will be appreciated that a variety of programming languages may be used.

As used herein, the term "image" refers to multi-dimensional data composed of discrete image elements (e.g., pixels for 2D images and voxels for 3D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, or a mapping to $R^3$, the present methods are not limited to such images, and can be applied to images of any dimension, e.g., a 2D picture or a 3D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

The terms "pixels" for picture elements, conventionally used with respect to 2D imaging and image display, and "voxels" for volume image elements, often used with respect to 3D imaging, can be used interchangeably. It should be noted that the 3D volume image is itself synthesized from image data obtained as pixels on a 2D sensor array and displayed as a 2D image from some angle of view. Thus, 2D image processing and image analysis techniques can be applied to the 3D volume image data. In the description that follows, techniques described as operating upon pixels may alternately be described as operating upon the 3D voxel data that is stored and represented in the form of 2D pixel data for display. In the same way, techniques that operate upon voxel data can also be described as operating upon pixels. In the following description, the variable x is used to indicate a subject image element at a particular spatial location or, alternately considered, a subject pixel. The terms "subject pixel" or "subject voxel" are used to indicate a particular image element as it is operated upon using techniques described herein. "Pixel" is typically used for discrete elements in data space, and "voxel" for elements in image space.

A framework for quality-driven image processing is described herein. In accordance with one aspect, one or more quality metrics (e.g., resolution, noise) are quantitatively measured directly from an intermediate image to guide or constrain image processing (e.g., iterative image reconstruction). The measurement of such quality metrics incorporates extra-modal structural information imparted by anatomical data (e.g., CT data).

In some implementations, anatomical data is used to derive zonal information for measuring the one or more quality metrics after each iteration and provide a criterion to stop the image reconstruction. The iterative image reconstruction may be performed to optimize the image resolution without overestimating the noise. For example, consider cardiac imaging where this framework segments the heart and obtains a template which is used to estimate both noise and resolution. Termination of the image reconstruction may occur when further iteration no longer provides improvement in resolution but results in deterioration of noise. Alternatively, the framework may request a resolution-noise trade off termination point. Accordingly, the present framework uses extra-modal information to enhance image reconstructions.

The data-driven quantitative approach of the present framework provides significant improvement in clinical usability, consistency in reconstructed image quality, quality control, standardization of image reconstruction and link of task-based image quality features and image reconstruction method dependent parameters. These and other exemplary features and advantages will be described herein.

FIG. 1 is a block diagram illustrating an exemplary system 100. The system 100 includes a computer system 101 for implementing the framework as described herein. In some implementations, computer system 101 operates as a standalone device. In other implementations, computer system 101 may be connected (e.g., using a network) to other machines, such as user device 103. In a networked deployment, computer system 101 may operate in the capacity of a server (e.g., thin-client server, such as syngo.via® by Siemens Healthineers®), a cloud computing platform, a client user machine in server-client user network environment, or as a peer machine in a peer-to-peer (or distributed) network environment.

In one implementation, computer system 101 comprises a processor or central processing unit (CPU) 104 coupled to one or more non-transitory computer-readable media 105 (e.g., computer storage or memory), a display device 109 (e.g., monitor) and various input devices 110 (e.g., mouse or keyboard) via an input-output interface 121. Computer system 101 may further include support circuits such as a cache, a power supply, clock circuits and a communications bus. Various other peripheral devices, such as additional data storage devices and printing devices, may also be connected to the computer system 101.

The present technology may be implemented in various forms of hardware, software, firmware, special purpose processors, or a combination thereof, either as part of the microinstruction code or as part of an application program or software product, or a combination thereof, which is executed via the operating system. In one implementation, the techniques described herein are implemented as computer-readable program code tangibly embodied in non-transitory computer-readable media 105. In particular, the present techniques may be implemented by image processing unit 106 and evaluation unit 107. Image processing unit 106 and evaluation unit 107 may be standalone components or integrated with another system, such as an electronic medical records (EMR) system.

Non-transitory computer-readable media 105 may include random access memory (RAM), read-only memory (ROM), magnetic floppy disk, flash memory, and other types of memories, or a combination thereof. The computer-readable program code is executed by CPU 104 to process data. As such, the computer system 101 is a general-purpose computer system that becomes a specific purpose computer system when executing the computer-readable program code. The computer-readable program code is not intended to be limited to any particular programming language and implementation thereof. It will be appreciated that a variety of programming languages and coding thereof may be used to implement the teachings of the disclosure contained herein.

The same or different computer-readable media 105 may be used for storing a database (or dataset) 108. Such data may also be stored in external storage or other memories.

The external storage may be implemented using a database management system (DBMS) managed by the CPU 104 and residing on a memory, such as a hard disk, RAM, or removable media. The external storage may be implemented on one or more additional computer systems. For example, the external storage may include a data warehouse system residing on a separate computer system, a picture archiving and communication system (PACS), or any other now known or later developed hospital, medical institution, medical office, testing facility, pharmacy or other medical patient record storage system.

Image processing unit 106 receives image data 119 from imaging modality 102. The imaging modality 102 may be, for example, a functional imaging modality that measures functional data of a functional process in the patient's body by using, for example, nuclear properties of matter. Examples of such functional imaging techniques include nuclear imaging such as Positron Emission Tomography (PET), Single Photon Computed Tomography (SPECT), functional magnetic resonance imaging (fMRI) and functional computed tomography (fCT). For these types of nuclear imaging, one administers a radioactive substance, usually a disease specific biomarker, to the patient and detects emitted radiation with a detector system, e.g., with a ring detector for PET or with one or several gamma cameras for SPECT. In general, the detector system provides functional data (e.g., raw data or preprocessed data) to the image processing unit 106.

Evaluation unit 107 receives anatomical data 149 from anatomical imaging modality 140 and image data from image processing unit 106 for quality evaluation. Examples of an anatomical imaging modality 140 include, but are not limited to, a computed tomography (CT) system (e.g., a transmission CT system) and a magnetic resonance (MR) imaging system.

User device 103 may include a computer (e.g., mobile computing device or personal tablet) and appropriate peripherals, such as a keyboard and display device, and can be operated in conjunction with the entire system 100. User device 103 may include, for example, an App that presents a graphical user interface that collects input data 120 for manipulating data processing and displays output data (e.g., final image). User input data may be received via an input device (e.g., keyboard, mouse, touch screen, voice or video recognition interface, etc.) implemented in the user device 103.

It is to be further understood that, because some of the constituent system components and method steps depicted in the accompanying figures can be implemented in software, the actual connections between the systems components (or the process steps) may differ depending upon the manner in which the present framework is programmed. Given the teachings provided herein, one of ordinary skill in the related art will be able to contemplate these and similar implementations or configurations of the present framework.

Figure 2:
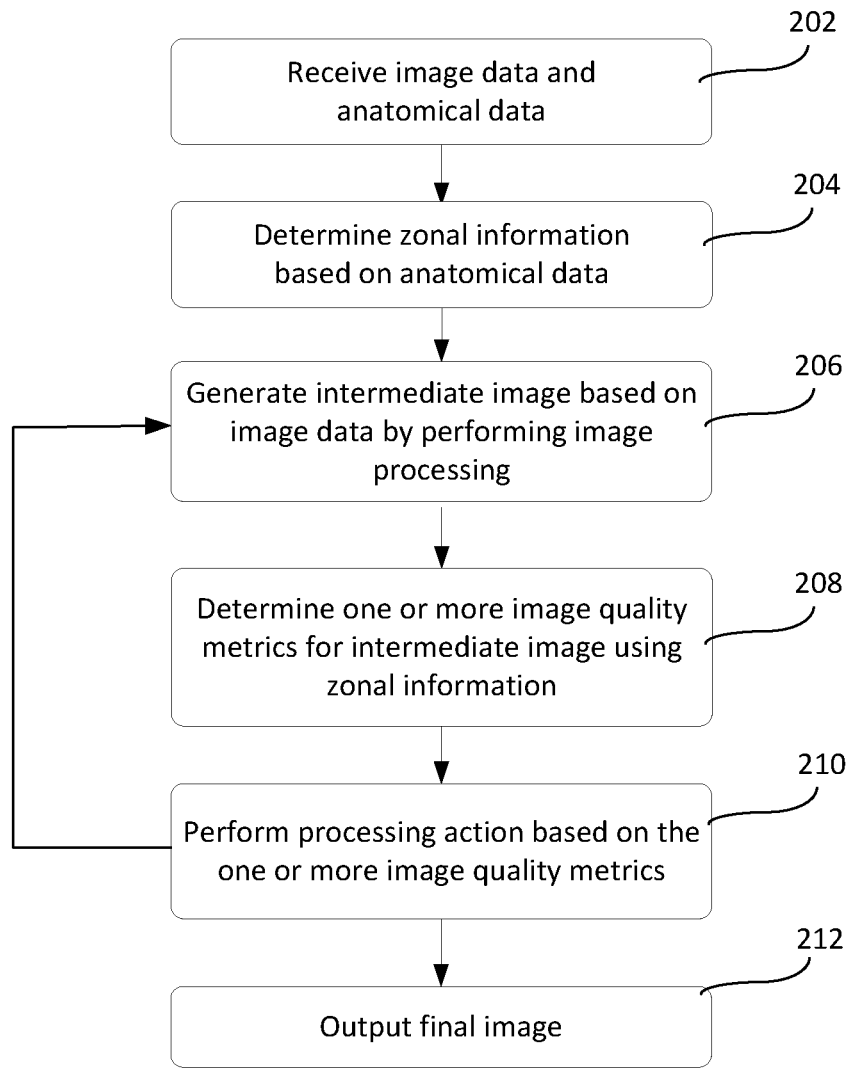
FIG. 2 shows an exemplary method of image processing by a computer system.

FIG. 2 shows an exemplary method 200 of image processing by a computer system. It should be understood that the steps of the method 200 may be performed in the order shown or a different order. Additional, different, or fewer steps may also be provided. Further, the method 200 may be implemented with the system 100 of FIG. 1, a different system, or a combination thereof.

At 202, image data and anatomical data of a region of interest are received. The region of interest may be a liver, lung, heart, brain, bone or other structures of interest identified for study. Image data may be derived from functional data received from, for example, imaging modality 102 or database 108. Functional data (e.g., SPECT, PET data) measures a functional process in the patient's body by using, for example, nuclear properties of matter. Other types of image data may also be used.

Anatomical data (e.g., computed tomographic or CT, magnetic resonance or MR data) may be received from, for example, anatomical imaging modality 140 or database 108. Anatomical data provides extra-modal structural information (e.g., shape, volume, thickness, density of tissue types) about the anatomy of the region of interest, so that the image space can be divided into uniform areas, templates or zones. For example, a CT image can provide support anatomical information based on the measured absorption of the imaging radiation. As another example, a measured MR image can provide high contrast information for soft tissue. Other types of anatomical data may also be used.

At 204, evaluation unit 107 generates zonal information based on the anatomical data. A "zone" is generally a template or region of points with uniform or similar features. A zone need not be an enclosed area, and can include multiple disjoint areas. One zone usually represents a target structure or tissue (e.g., bone, kidney) of the image data, while the area (e.g., soft tissue) surrounding the examined structure is usually referred to as a Null zone and does not contribute to the functional signal. The information about how the image space is separated into zones is referred to as "zonal information". In some implementations, the zonal information includes one or more smoothed zones and functions defining the boundary and interior of each zone. The zonal information may also include a label of the zone (e.g., left kidney, skeleton).

Figure 3:
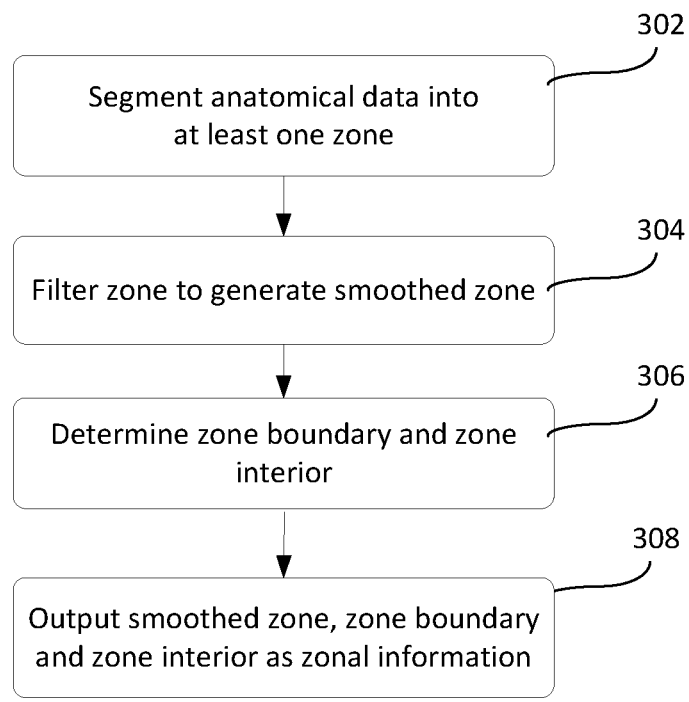
FIG. 3 shows an exemplary method of deriving zonal information.

FIG. 3 shows an exemplary method 204 of deriving zonal information. It should be understood that the steps of the method 204 may be performed in the order shown or a different order. Additional, different, or fewer steps may also be provided. Further, the method 204 may be implemented with the system 100 of FIG. 1, a different system, or a combination thereof.

At 302, evaluation unit 107 segments the anatomical data into at least one zone. The at least one zone may represent, for example, a bone area. In some implementations, segmentation is performed based on an absorption coefficient map (i.e., µ-map) that is derived from the anatomical data (e.g., CT data). Similar absorption coefficients (µ-values) derived from a CT scan can be used to determine zones. Alternatively, segmentation may be performed directly based on the anatomical data. The zone can be represented by a zone-function zone that assigns values greater than zero to all points at least partly affiliated with the respective zone. The zone-function zone can be a pure functional presentation, indicating position(s) and shape(s) in the image space.

At 304, evaluation unit 107 applies a smoothing filter function G to the zone-function zone to generate a smoothed zone (e.g., $zone_c^{smoothed}$=zone*G). The smoothed zone provides a high-resolution template for comparison with the same slices in the corresponding intermediate image, as will be described later. Exemplary smoothing filter functions include, but are not limited to, a pixon filter, a Wiener filter, a wavelet filter, a Gaussian filter, a median filter, or a combination thereof.

At 306, evaluation unit 107 determines the zone boundary and zone interior (i.e., points inside the zone) of the zone. In some implementations, the zone boundary and zone interior are determined by applying the Sobel operator to the zone-function zone. For example, the boundary of the zone in u and v directions ($\sigma_u^{zone}$, $\sigma_v^{zone}$) may be obtained as follows:

$$\sigma_u^{zone} = zone * p'_u \quad (1)$$

$$\sigma_v^{zone} = zone * p'_v \quad (2)$$

wherein $p'_u$ and $p'_v$ are the derivative kernels of the Sobel operator for the u and v directions. The interior of the zone may be determined by, for example, a watershed algorithm or other suitable algorithm.

The zone boundary may be represented by, for example, an edge-response function $\nabla$zone, which assigns values between 0 and 1 for points on the boundary of the zone, so as to allow a smooth transition between zones. A zone interior may be represented by, for example, a function $zone^1$, which assigns the value 1 to points within the zone having a μ-value within a predefined range of μ-values and a value of 0 to points outside that range.

Figure 4A:
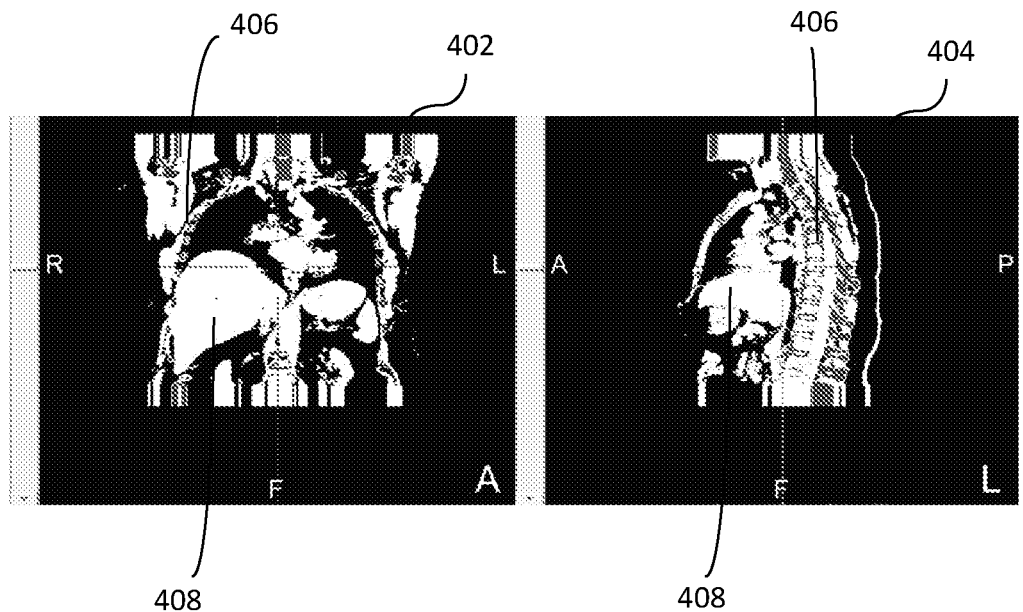
FIG. 4a shows exemplary CT images of a human chest.
Figure 4B:
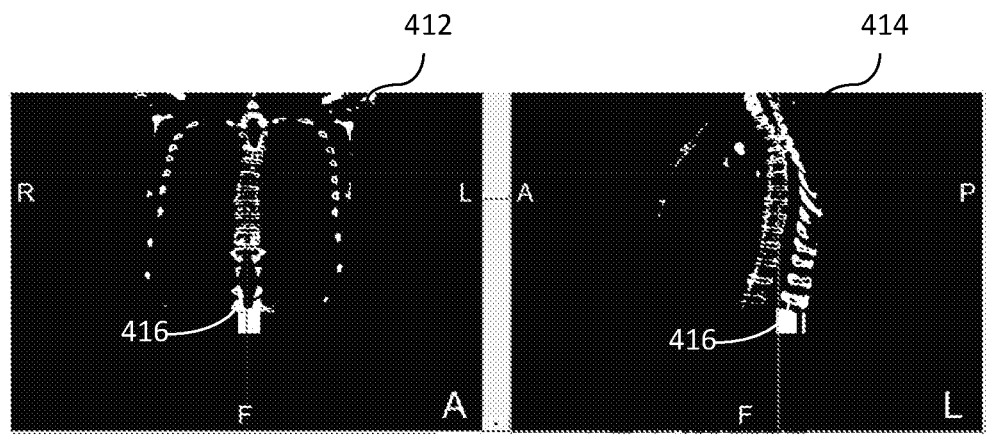
FIG. 4b shows exemplary CT images in which the boundaries of the bone area are detected.

FIG. 4a shows exemplary CT images 402 and 404, which present a coronal view and sagittal view respectively of a human chest. CT images 402-404 are segmented to define a bone area (zone) 406 and soft tissue area 408 that can be used to estimate the noise level in the reconstructed image data. FIG. 4b shows exemplary CT images 412 and 414 in which the boundaries (or edges) 416 of the bone area are detected. The bone boundaries 416 may be used to measure resolution recovery in bone image reconstruction.

Returning to FIG. 3, at 308, evaluation unit 107 outputs the smoothed zone ($zone_{\sigma_n}^{smoothed}$), zone boundary ($\nabla$zone), and zone interior ($zone^1$) as zonal information.

Returning to FIG. 2, at 206, image processing unit 106 performs image processing based on the image data to generate one or more intermediate images. Image processing generally refers to any operation or sequence of operations performed on image data. Image processing may include, for example, iterative image reconstruction. Other types of image processing, such as image smoothing, are also possible. Iterative image reconstruction methods, such as algorithms based on maximum likelihood, algorithms based on an ordered subset expectation maximization, algorithms based on a non-negative least square fit, algorithms based on an ordered subset non-negative least square fit, and algorithms based on a pixon method, iteratively fit image models to the measured functional data to improve the quality of the final reconstructed image. Within the iterative reconstruction algorithm, an iteration step is defined as a single pass through a set of data subsets. For each data subset, one may use the current estimated image to initialize the application of the expectation maximization. The result of a reconstruction algorithm is a reconstructed intermediate image that is fit to, for example, the measured functional data set according to the rules of the algorithm.

At 208, evaluation unit 107 determines one or more image quality metrics for the intermediate image using the zonal information. The one or more quality metrics characterize the quality of the estimated reconstructed image data using the zonal information. In some implementations, the one or more quality metrics characterize noise and resolution. Other types of quality metrics may also be determined. Additionally, a single quality metric or more than two quality metrics may also be determined.

One exemplary quality metric is noise, which characterizes noise in the intermediate image within the interior of the zone. The noise metric may be obtained by determining the ratio of standard deviation (std) over the mean within a zone. The noise metric may be represented as follows:

$$noise = std[data * zone^1]/mean(data * zone^1) \quad (3)$$

wherein std represents the standard deviation function, mean represents the mean function, $zone^1$ represents the zone interior function and data represents the intermediate image data.

Another exemplary quality metric is $\sigma_{resolution}$, which characterizes the resolution of the intermediate image at the boundary of the zone. The resolution metric $\sigma_{resolution}$) may be obtained by estimating a matched filter, which may be determined by minimizing a L2 or L1 metric in image space. The zonal information derived from the anatomical data may be used to compare to the corresponding slices in the intermediate image data. The resolution quality metric ($\sigma_{resolution}$) may be represented as follows:

$$\sigma_{resolution} = \underset{\sigma_n}{\arg\min} \frac{\sum (zone_{\sigma_n}^{smoothed} - data)^2 \cdot \nabla zone}{\sum data \cdot \nabla zone} \quad (4)$$

wherein $zone_{\sigma_n}^{smoothed}$ drepresents the smoothed zone function, $\nabla$zone represents the zone boundary function and data represents the estimated intermediate image data.

At 210, evaluation unit 107 performs a processing action based on the one or more quality metrics to generate a final image. The processing action may be, for example, stopping (or continuing) the iterative image reconstruction process in response to the one or more quality metrics satisfying a predetermined stop-criterion or changing the image processing operation.

In some implementations, evaluation unit 107 determines whether the one or more quality metrics satisfy a predetermined stop-criterion for stopping the iterative image reconstruction. The predetermined stop-criterion may be defined based on one or more predetermined threshold values. For example, an exemplary stop-criterion is satisfied if the resolution quality metric ($\sigma_{resolution}$) is greater than the predetermined threshold value $K_1$ and the noise quality metric (noise) is less than the predetermined threshold value $K_2$. The selection of the predetermined thresholds $K_1$ and $K_2$ may be determined by expert users, depending on the application. Advantageously, such stop-criterion ensures that the image reconstruction is terminated before it starts modeling the noise without improving the reconstruction. By using anatomical information to estimate noise and edge reconstruction, resolution quality may be maximized while keeping the reconstruction of noise to a minimum.

If the stop-criterion is not satisfied, image processing unit 106 increments the current iteration to the next iteration and continues to perform iterative image reconstruction (or image processing) for the next iteration at 206. If the stop-criterion is satisfied, evaluation unit 107 stops or terminates the iterative image reconstruction and outputs the final image at 212. The final image is the intermediate image of the final iteration of the image reconstruction. The final image may be displayed at, for example, user device 103.

Figure 5A:
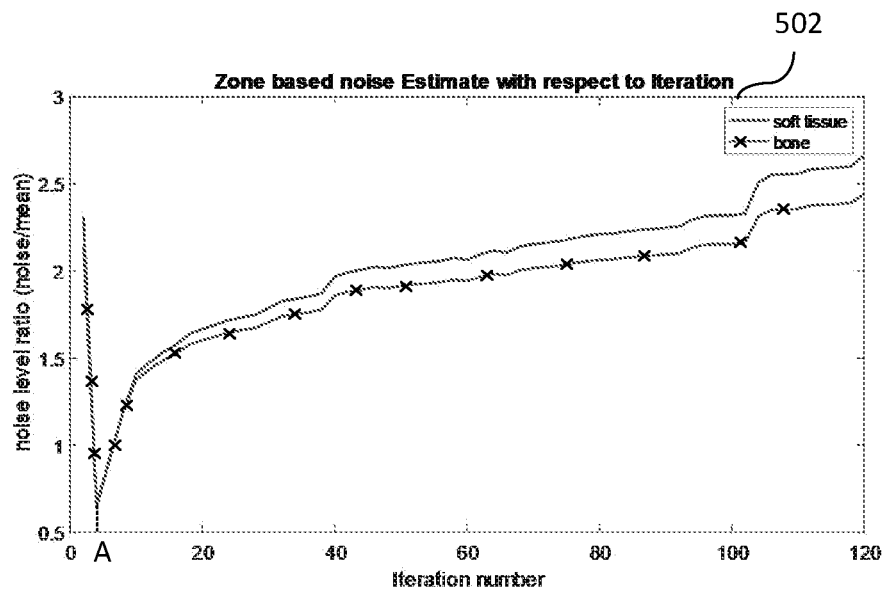
FIG. 5a shows an exemplary graph illustrating zone-based estimated noise with respect to iterations of the image reconstruction.
Figure 5B:
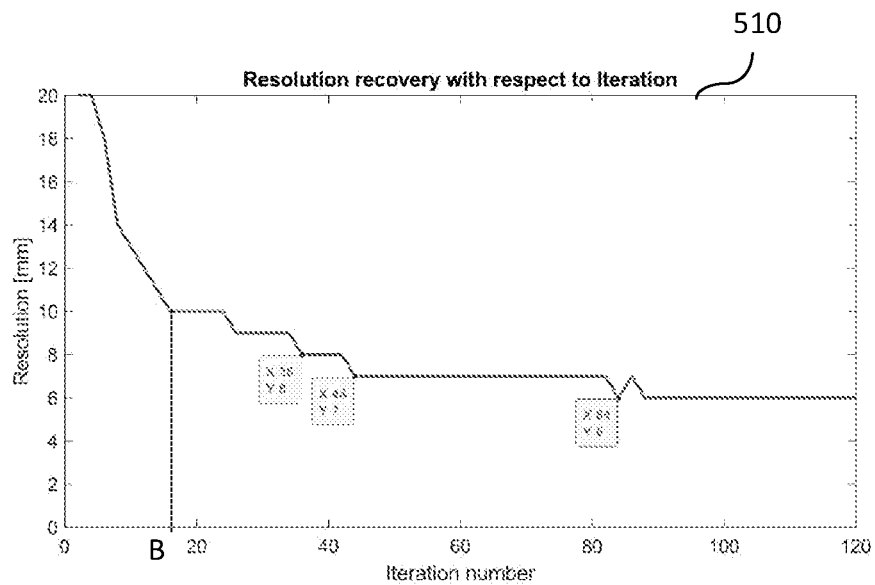
FIG. 5b shows another exemplary graph illustrating resolution recovery with respect to iterations of the image reconstruction.

FIG. 5a shows an exemplary graph 502 illustrating zone-based estimated noise with respect to iterations of the image reconstruction. Noise is estimated for soft tissue and bone zones. The noise level ratios for both soft tissue and bone zones decrease rapidly before iteration A and then increase fairly steadily after iteration A. FIG. 5b shows another exemplary graph 510 illustrating resolution recovery with respect to iterations of the image reconstruction. The resolution drops rapidly before iteration B and then decreases at a slower rate thereafter.

While the present framework has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

What is claimed is:

1. A system for iterative image reconstruction, comprising:
   a non-transitory memory device for storing computer-readable program code; and
   a processor in communication with the non-transitory memory device, the processor being operative with the computer-readable program code to perform operations including
   receiving image data and anatomical data of a region of interest,
   generating zonal information based on the anatomical data, wherein the zonal information includes at least one zone-function that defines at least one smoothed zone of the anatomical data,
   performing the iterative image reconstruction based on the image data to generate reconstructed image data,
   determining one or more image quality metrics for the reconstructed image data using the zonal information, wherein the one or more image quality metrics are based on the at least one zone-function and quantitatively measure quality of the reconstructed image data within or at a boundary of the at least one smoothed zone,
   in response to the one or more image quality metrics satisfying a stop-criterion, terminating the iterative image reconstruction, and
   outputting a final image generated by the iterative image reconstruction.

2. The system of claim 1 wherein the image data comprises functional data.

3. The system of claim 1 wherein the anatomical data comprises computed tomographic data or magnetic resonance data.

4. The system of claim 1 wherein the one or more image quality metrics comprise a noise metric, a resolution metric, or a combination thereof.

5. A method of image processing, comprising:
   receiving image data and anatomical data of a region of interest;
   determining zonal information based on the anatomical data, wherein the zonal information includes at least one zone-function that defines at least one smoothed zone of the anatomical data;
   generating an intermediate image based on the image data by performing image processing;
   determining one or more image quality metrics for the intermediate image using the zonal information wherein the one or more image quality metrics are based on the at least one zone-function and quantitatively measure quality of the intermediate image within or at a boundary of the at least one smoothed zone; and
   performing a processing action based on the one or more image quality metrics to generate a final image.

6. The method of claim 5 wherein determining the zonal information based on the anatomical data comprises:
   segmenting the anatomical data into at least one zone;
   applying a smoothing filter function to the at least one zone to generate the at least one smoothed zone; and
   determining the boundary and a zone interior of the at least one smoothed zone.

7. The method of claim 6 wherein applying the smoothing filter function comprises applying a pixon filter, a Wiener filter, a wavelet filter, a Gaussian filter, a median filter, or a combination thereof.

8. The method of claim 6 wherein determining the boundary and the zone interior of the at least one zone comprises applying a Sobel operator.

9. The method of claim 5 wherein generating the intermediate image based on the image data by performing the image processing comprises performing iterative image reconstruction.

10. The method of claim 5 wherein determining the one or more image quality metrics for the intermediate image using the zonal information comprises determining a noise metric.

11. The method of claim 10 wherein determining the noise metric comprises determining a ratio of a standard deviation over a mean within at least one zone.

12. The method of claim 5 wherein determining the one or more image quality metrics for the intermediate image using the zonal information comprises determining a resolution metric that characterizes resolution of the intermediate image at the boundary of the at least one smoothed zone.

13. The method of claim 12 wherein determining the resolution metric comprises estimating a matched filter.

14. The method of claim 5 wherein performing the processing action based on the one or more image quality metrics comprises stopping an iterative image reconstruction in response to the one or more image quality metrics satisfying a predetermined stop-criterion.

15. The method of claim 14 further comprises determining whether the one or more image quality metrics meet one or more predetermined threshold values.

16. The method of claim 15 wherein determining whether the one or more image quality metrics meet the one or more predetermined threshold values comprises determining whether a resolution metric is greater than the one or more predetermined threshold values.

17. The method of claim 15 wherein determining whether the one or more image quality metrics meet the one or more predetermined threshold values comprises determining whether a noise metric is less than the one or more predetermined threshold values.

18. One or more non-transitory computer-readable media embodying instructions executable by a computer to perform operations comprising:
   receiving image data and anatomical data of a region of interest;
   determining zonal information based on the anatomical data, wherein the zonal information includes at least one zone-function that defines at least one smoothed zone of the anatomical data;
   generating an intermediate image based on the image data by performing image processing;
   determining one or more image quality metrics for the intermediate image using the zonal information, wherein the one or more image quality metrics are based on the at least one zone-function and quantitatively measure quality of the intermediate image within or at a boundary of the at least one smoothed zone; and
   performing a processing action based on the one or more image quality metrics to generate a final image.

19. The one or more non-transitory computer-readable media of claim 18 wherein the one or more image quality metrics comprise a noise metric.

20. The one or more non-transitory computer-readable media of claim 18 wherein the one or more image quality metrics comprise a resolution metric that characterizes resolution of the intermediate image at the boundary of the at least one smoothed zone.

* * * * *